United States Patent [19]
Sintov et al.

[11] Patent Number: 5,425,953
[45] Date of Patent: Jun. 20, 1995

[54] POLYMER COMPOSITION FOR TOOTH BLEACHING AND OTHER DENTAL USES THEREOF

[75] Inventors: Amnon Sintov; Rami Kariv, both of Jerusalem, Israel

[73] Assignee: Perio Products Limited, Jerusalem, Israel

[21] Appl. No.: 871,969

[22] Filed: Apr. 22, 1992

[30] Foreign Application Priority Data

Apr. 23, 1991 [IL] Israel ......................... 97930

[51] Int. Cl.⁶ ............................................. A61K 7/20
[52] U.S. Cl. ..................... 424/404; 424/52; 424/53
[58] Field of Search ........................ 424/401, 52, 53

[56] References Cited

U.S. PATENT DOCUMENTS

| | | | |
|---|---|---|---|
| 4,155,738 | 5/1979 | Boghosian | 71/25 |
| 4,315,779 | 2/1982 | Heyd et al. | 106/35 |
| 4,592,487 | 6/1986 | Simon et al. | 222/94 |
| 4,713,243 | 12/1987 | Schiraldi et al. | 424/151 |
| 4,983,380 | 1/1991 | Yarborough | 424/52 |
| 5,000,942 | 3/1991 | Libin . | |
| 5,160,737 | 11/1992 | Friedman et al. | 424/401 |
| 5,171,564 | 12/1992 | Nathov et al. | 424/614 |
| 5,256,402 | 10/1993 | Principe et al. | 424/613 |

FOREIGN PATENT DOCUMENTS

| | | | |
|---|---|---|---|
| 0241179A1 | 10/1987 | European Pat. Off. | A61K 9/70 |
| 90/01046 | 8/1990 | European Pat. Off. . | |
| 0446524A2 | 9/1991 | European Pat. Off. | A61K 7/20 |
| WO89/10745 | 11/1989 | WIPO | A61K 31/60 |
| WO90/09165 | 8/1990 | WIPO | A61K 7/16 |

OTHER PUBLICATIONS

Epstein, S., *Oral Surg.* 32(6):886–890 (1971).
Haywood, V. B., et al., *Quintessence Int.* 20:173–176 (1989).
Stindt, D. J. et al., *Compend. Contin. Educ. Dent.* 10(9):514–519.
Wennström, J., et al., *Jour. Clin. Periodontol.* 6:115–130 (1979).
*Am. Hosp. Formul. Serv., Carbamide Peroxide*, Dialog file No. 229.
Rodu, B. et al., "Performance of a hydroxypropyl cellulose film former in normal and ulcerated oral mucosa," *Oral Surg.* 65(6):699–703 (Jun. 1988).

*Primary Examiner*—Thurman K. Page
*Assistant Examiner*—Peter F. Kulkosky
*Attorney, Agent, or Firm*—Sterne, Kessler, Goldstein & Fox

[57] ABSTRACT

A unique storage stable liquid polymer composition is described containing a water-soluble, low viscosity cellulosic polymer, bleaching agent and vehicle. Also, described are uses of this composition for the bleaching of teeth, treatment of dental plaque, gingivitis, and other oral and periodontal diseases that respond to chemical oxidizing agents.

59 Claims, 10 Drawing Sheets

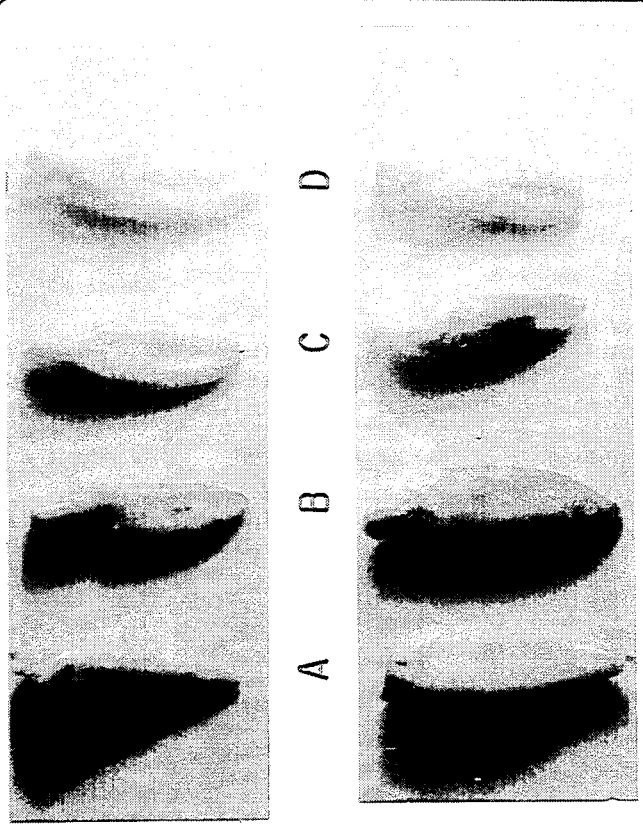
FIG. 1A
BEFORE TREATMENT
NICOTINE STAINING
BLOOD STAINING
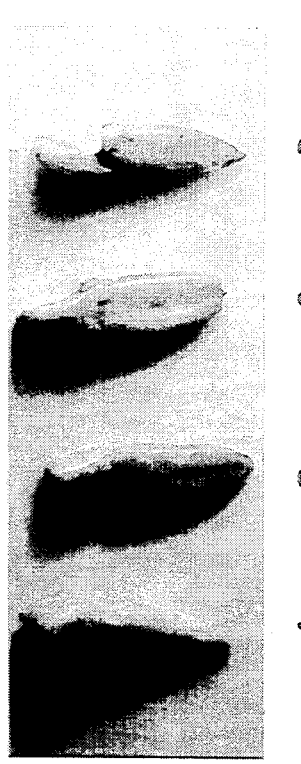
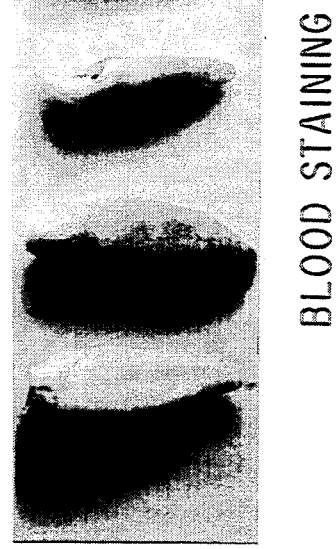
FIG. 1B
7TH DAY OF TREATMENT
NICOTINE STAINING
BLOOD STAINING

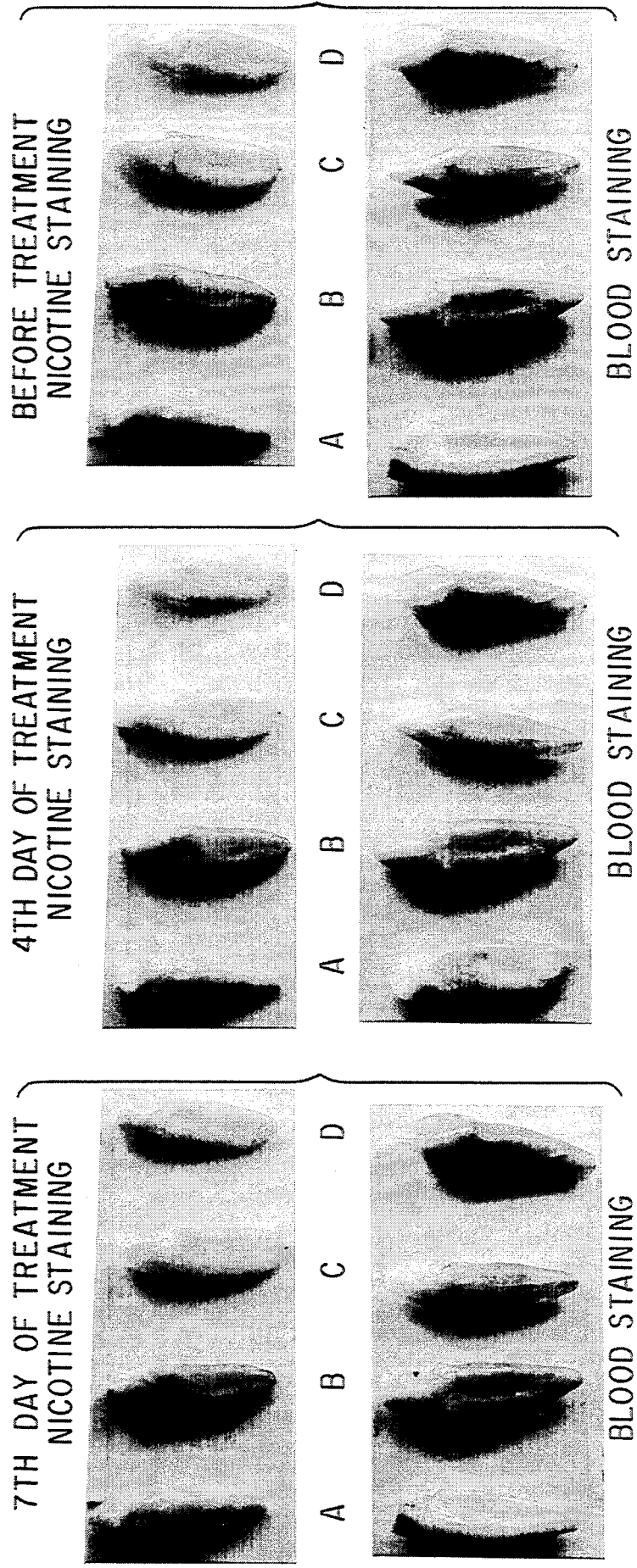

BEFORE TREATMENT

A  B  C  D

CHLORHEXIDINE STAINING

4TH DAY OF TREATMENT

A  B  C  D

CHLORHEXIDINE STAINING

7TH DAY OF TREATMENT

A  B  C  D

CHLORHEXIDINE STAINING

BLOOD STAINING
BEFORE TREATMENT

4TH DAY OF TREATMENT
BLOOD STAINING

BLOOD STAINING
7TH DAY OF TREATMENT

CHLORHEXIDINE STAINING
BEFORE TREATMENT

4TH DAY OF TREATMENT
CHLORHEXIDINE STAINING

CHLORHEXIDINE STAINING
7TH DAY OF TREATMENT

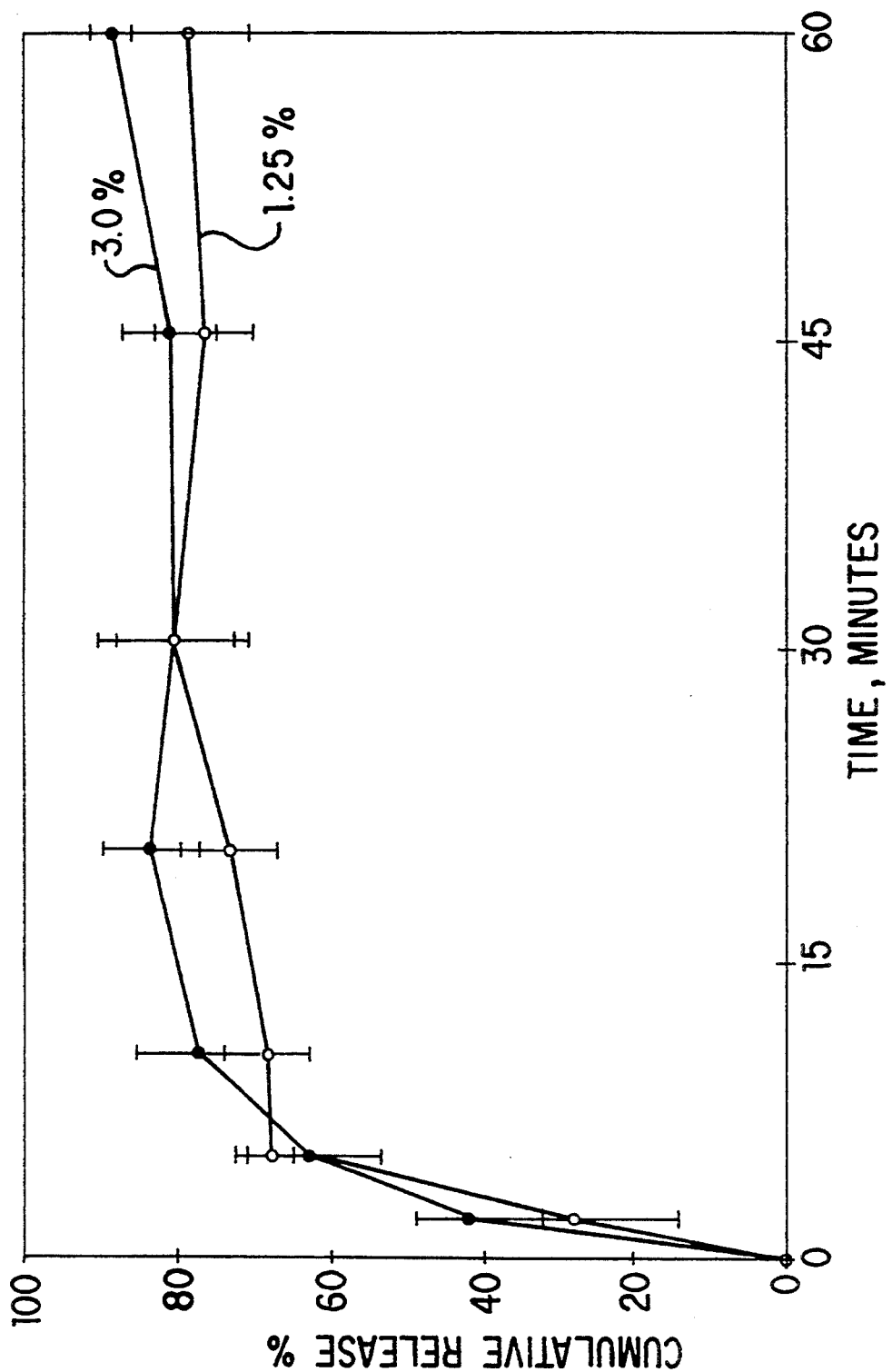

VOLUNTEER #194
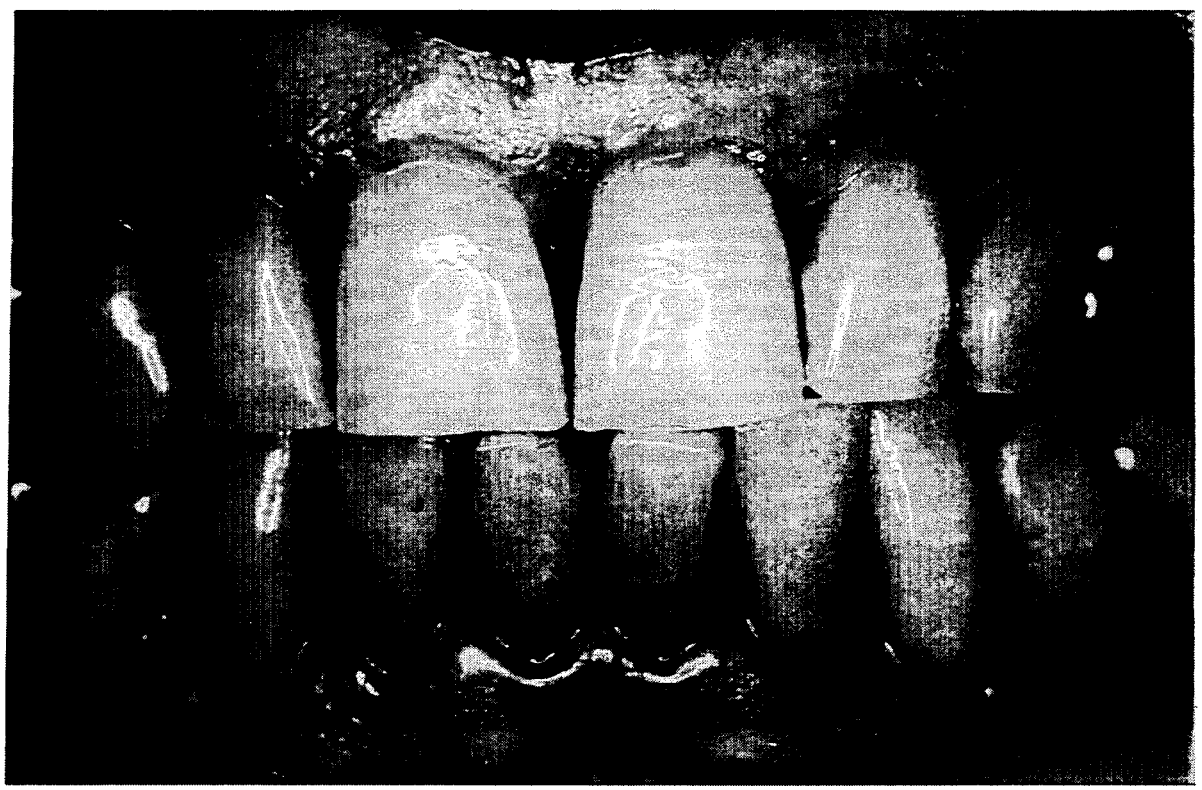
t = 0
FIG. 9A
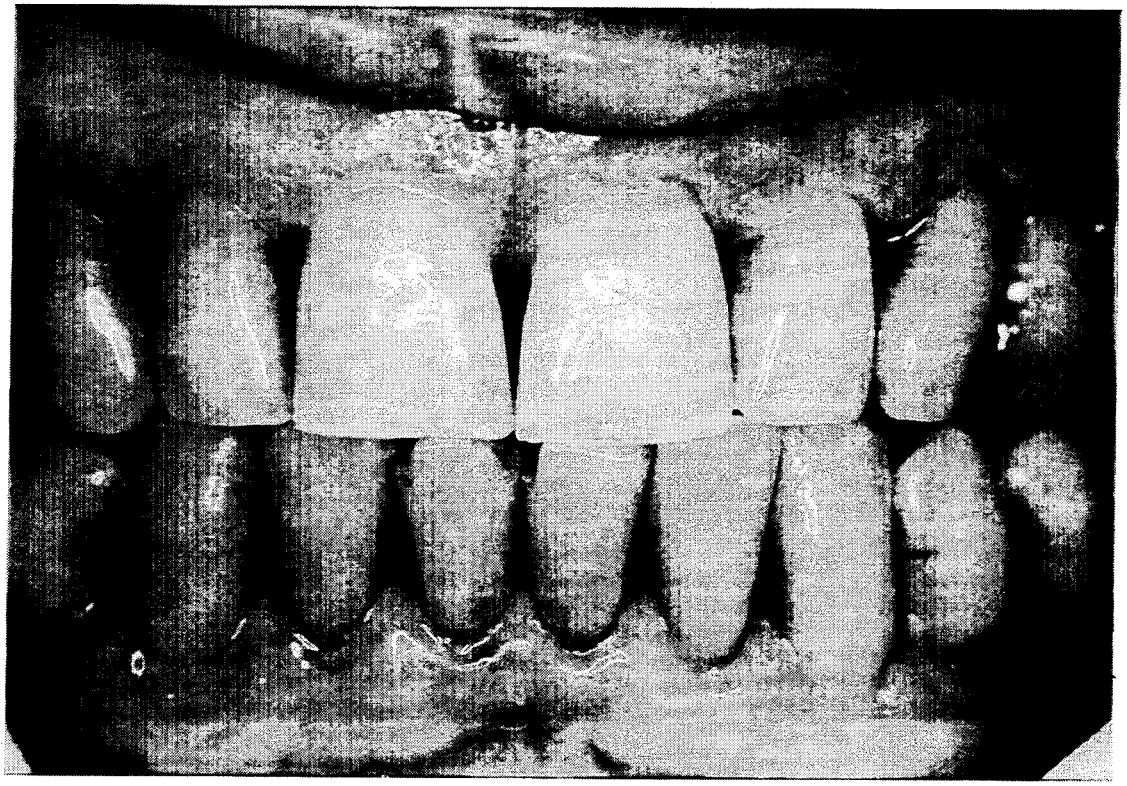
t = 4 WEEKS

VOLUNTEER #139
t = 0
FIG. 10A
t = 4 WEEKS

POLYMER COMPOSITION FOR TOOTH BLEACHING AND OTHER DENTAL USES THEREOF

FIELD OF THE INVENTION

The invention is in the field of liquid polymer compositions which may be used in the bleaching of discolored teeth or prevention of tooth discoloration. The composition of the invention provides the short-term sustained-release of an oxidizing agent, preferably a peroxide compound, which removes stains from discolored teeth and is also capable of preventing tooth discoloration. The composition of the invention is also useful for the prevention of dental plaque, the treatment of gingivitis and the treatment of other oral and dental diseases.

BACKGROUND OF THE INVENTION

Dental Bleaching

Tooth discoloration is either extrinsic—on the enamel, or intrinsic—penetrating the tooth dentin. Tea, coffee, nicotine from cigarette smoking and mouth rinses containing active antibacterial agents such as chlorhexidine and cetylpyridinium chloride may cause superficial tooth staining. This type of discoloration is more affected when the dentin is exposed, such as in the case of cracks in the enamel, due to both higher affinity for the discoloring substances to dentin than to enamel and their deeper penetration, so that their removal is extremely difficult. Intrinsic staining is much more complicated because it may involve the dentin more than the enamel. Examples of factors affecting intrinsic discoloration are tetracycline administration during tooth calcification, fluorosis, jaundice during tooth development, trauma which causes internal bleeding, and endodontic materials.

Tooth bleaching has gained increasing interest over the past decade, with the growing awareness of aesthetic dentistry. Modified techniques for whitening discolored teeth have been developed. These techniques involve treatment both at the dental clinic and at home by the patient. Treatment currently carried out by the dentist generally involves acid etching of the enamel with 32% phosphoric acid, followed by bleaching, by applying hydrogen peroxide (30%) to the tooth surfaces. This is followed by application of heat for 20 to 30 minutes, with a heat element or a heat lamp. With severely discolored teeth this method of bleaching is not totally effective, and veneering techniques with concomitant use of opaquers are then necessary. The common bleaching techniques thus typically involve a considerable amount of dental chair time, at a potentially significant cost to the patient.

Home treatment involves the use of 10% carbamide peroxide (urea peroxide) (Haywood et al., *Quint. Int.* 20(3): 173–176 (1989)). The patient wears a thin vacuform matrix over the teeth, and a reduced concentration of peroxide (which is within safety limits approved by the FDA) is placed within the appliance. The use of 10% urea peroxide as a home treatment is aimed at being significantly time- and cost-saving for the patient (Federal Register, Vol. 47, N9. 101, p. 22, 875 (1982)). Haywood ibid. also stressed that using the nightguard, rather than the known rubber dam technique, eliminates the necessity of the pretreatment etching step. It is well known that etching with phosphoric acid or other acids may alter the surface texture of the teeth. Said authors suggest the use of phosphoric acid only as a preservative in the 10% urea peroxide solution, which also contains carbomer 940, glycerine, flavors, phenacetin and trolamine (Proxigel®, Reed & Carnick, Piscataway, N.J.).

Additional home-use tooth bleaching products have also been recently described (*Clinical Res. Assoc.* 13: 7 (July 1989)). This report describes various commercially available products, all containing 10% carbamide peroxide. DENTA-LITE® (Challenge Products, Osage Beach, Mo.) is a gel bleaching preparation sold to dentists only. Its recommended use is to wear a tray for at least 14 hours per day, changing the bleach every 1–2 hours for 1 week or longer. DENTL-BRITE® (Cura Pharmaceutical, Jacksonville Fla.) is a bleaching preparation sold to dentists only. Its recommended use is to wear a tray for 18 hours per day, changing the bleach every 2 hours for 2 weeks. GLY-OXIDE® (Marion Laboratories, Kansas City, Mo.) is an off-the-counter preparation intended for oral antiseptic uses only. It was not reported as a teeth bleaching agent. REMBRANDT LIGHTEN® (Dean-Mat, Santa Maria, Calif.) is a gel containing 10% carbamide peroxide and a dentifrice. The gel is used by frequent daily brushes or worn in a mouthguard for at least 12 hours per day. These products have not been reported as bleaching agents. ULTRA LITE® (Ultra Lite, Inc., Orange Park, Fla.) is a bleaching preparation sold to dentists only. Its recommended use is to wear a tray at least 18 hours per day, changing the bleach every 2 hours for 2 weeks or longer. WHITE & BRITE® (Omnii International, St. Petersburg, Fla.) is a bleaching preparation sold to dentists only. Its recommended use is to wear a tray 18–20 hours daily, changing the bleach every 2–2.5 hours for about 2 weeks. In this report, the PROXIGEL® preparation referred to above is also mentioned as an antiseptic and not as a bleaching preparation. This product was originally aimed at improving oral hygiene particularly by removing dental plaque, and is in the form of a solution.

Recently a more sophisticated product has been introduced on the market. This product, sold under the name OPALESCENCE® (Ultradent Products, Inc., Salt Lake City, Utah) (U.S. and foreign patent applications pending), is presented by its manufacturer as a sustained-release carbamide peroxide gel. This feature increases the efficacy of the product and reduces the appliance wearing time to only at night, which in turn is believed to increase patient compliance. Nevertheless, since the major problem is the appliance, the advantages described with the OPALESCENCE® product do not totally overcome the problem of patient compliance.

Patient compliance is the major problem (Goldstein et al., *Quint. Int.* 20: 729 (1989)). The need to wear an appliance for a long time, 12–20 hours per day, discourages many patients from using these products. Others stop care before desired results are achieved (CRA 13(7) (1989)). Other major problems associated with the mouth guard, as reported in said CRA publication, are speech difficulties, irritation to teeth and gingiva, allergic reactions such as tissue swelling, sore throat, bite interference from extended tray use and minor tooth movement. Also said reports refer to possible side effects due to swallowing various ingredients in the formulations over days or weeks, depending on the product and the time worn per day.

One of the primary advantages of the composition of the present invention over this prior art, as will become evident from the detailed description, is patient compliance. It eliminates the necessity of wearing a mouthguard, being a film-forming composition which closely adheres to the dentin layer. This being the case, smaller quantities of chemicals can be applied to the teeth, which is another important advantage.

The use of water-soluble cellulosic polymers, and more particularly, hydroxypropyl cellulose, has been described. For example, WO 90/01046 discloses a composition for in situ formation of medicament films, inter alia, in the oral cavity, comprising hydroxypropyl cellulose (HPC), a weak organic acid (which reaches with the HPC to form a reaction product which is soluble in a non-toxic volatile solvent for the HPC and the reaction product, but is insoluble in body fluids at body temperatures), said non-toxic volatile solvent and a separate medicinal component. This publication does not disclose application for tooth bleaching. According to this publication, the films, once formed, simply redissolve upon a further application of the composition to the same site. The film-forming composition according to the present invention simply disintegrates within reactively short periods at time, but not before the release of the bleaching agent has been completed.

Another oral composition for treatment of dental hypersensitivity is disclosed in U.S. Pat. No. 4,645,662 to Nakashimi et al. This publication discloses compositions containing aluminum and a carboxylate compound. Some of the examples describe such compositions also containing hydroxyethyl cellulose, for example, hydroxyethyl- and hydroxypropyl celluloses. These ingredients are described as binders, effective only together with carrageenan, for compositions in the form of paste. This patent does not suggest the liquid polymeric short-term sustained-release bleaching preparation of the present invention.

U.S. Pat. No. 4,713,243 to Schiraldi et al. discloses a bioadhesive extruded film particularly for intra-oral controlled release delivery of a medicament, comprising, inter alia, hydroxypropyl cellulose with an ethylene oxide homopolymer. This extruded preparation is essentially different from the presently claimed in situ film-forming preparation.

U.S. Pat. No. 4,315,779 to Heyd et al. discloses a non-adhesive gel composition for use in improving the fit and adaptation of dentures to the oral cavity, comprising, inter alia, a hydrophilic cellulosic polymer, for example hydroxypropyl cellulose. Also this publication does not suggest the presently claimed dental bleaching composition.

In addition, tooth bleaching preparations contain hydrogen peroxide or peroxy compounds are known in the art. Most of the known preparations are dentifrices, some are gel preparations, as described above.

The stability of urea peroxide is cited in several patents. Japanese Patent 87 280298 A2 and 62 20298 disclose the use of sodium citrate as a stabilizer for urea peroxide in the powder form. U.S. Pat. No. 4,155,738 discloses the use of lignin sulphonide for stabilizing hydrogen peroxide or urea peroxide in a fertilizer composition. Another way of stabilizing urea peroxide in glycerol solution is with succinate anhydride (GB 2,219,504). The use of EDTA for stabilizing urea peroxide in solution has also been disclosed in U.S. Pat. No. 3,624,331, which discloses the stabilizing of urea peroxide for cosmetic use, and in Japanese Patent DM375220.

The use of carbamide peroxide or hydrogen peroxide to treat gingivitis or to prevent dental plaque is well established in the literature. Hydrogen peroxide is recognized as an antimicrobial agent. It is especially useful against anaerobic bacteria, since these cannot produce catalases, which decompose hydrogen peroxide. (Stindt, D. J. et al., *Compend. Contin. Educ. Dent.* 10: 514–519 (1989). This antimicrobial effect makes hydrogen peroxide a candidate for preventing dental plaque and gingivitis.

However, results of in vivo studies are contradictory. On one hand, it has been demonstrated that mouthwash, containing hydrogen peroxide, prevents plaque and reduces gingivitis (Turner in: Block, S. S., ed., *Disinfection, Sterilization, Preservation*, Philadelphia, Lea and Febiger, pub., p. 240, (1983); Greenstein and Redman, *Compendium of Continuing Education in Dentistry* 8: 348–360 (1986), Shipman et al., *J. Priodontol.* 42: 283–285 (1971) and Wennstron et al., *J. Clin. Priodontol.* 6: 115–130 (1979)). On the other hand, Zinner et al., *J. Preven. Dentistry* 2: 13–17 (1980) found no significant reduction in plaque and gingivitis when compared to control groups. One of the possible explanations for this discrepancy is the rapid rate of decomposition of hydrogen peroxide caused by catalases fouled in the oral cavity. Hence a need exists for a more reliable method for the delivery of oxidizing agents for the prevention of plaque and reduction of gingivitis.

SUMMARY OF THE INVENTION

In order to overcome the above drawbacks with the bleaching compositions and treatments known in the art, the present inventors have now developed a composition that has many advantages. The liquid polymer composition of the present invention contains one or more chemical oxidizing agents in a highly stabilized form, and a liquid cellulosic polymer. The liquid polymer composition of the present invention optionally contains, a stabilizing additive, such as an edetic salt. Upon application to a tooth or other biological surface, the liquid polymer composition of the invention rapidly forms a film that adheres to such surface. This film provides a highly effective delivery matrix for the release of the oxidizing agents contained therein to the tooth or biological surface.

BRIEF DESCRIPTION OF THE FIGURES

The file of this patent includes drawings executed in color.

FIG. 1. FIG. 1A (Photograph I—Before Treatment) and FIG. 1B (Photograph II—After Treatment) show the effect of bleaching (oxidizing) with liquid polymer containing 1.25% ("C" teeth) and 3% ("D" teeth) carbamide peroxide on discolored teeth. Treatment was for 7 days. Clean teeth are shown in group "A." Control stained teeth are shown in group "B." Teeth treated with carbamide peroxide as described above are shown in groups "C" and "D." Teeth stained with tobacco (teeth "B-D" in the upper row in each photograph) or blood (teeth "B-D" in the lower row in each photograph) are presented.

FIG. 2. FIGS. 2A–2C (Photographs I, II, III, respectively): show the effect of bleaching with 3% carbamide peroxide liquid polymer of the invention (teeth "C") and the same amount of peroxide in solution (teeth "D") on discolored teeth after treatment for 4 and 7 days. FIG. 2A shows the teeth after seven days of treatment; FIG. 2B shows the teeth after 4 days of treatment; and FIG. 2C shows the teeth before treatment. Each photograph compares clean teeth (teeth "A"), and stained teeth (teeth "B-D"). Teeth "B" are the controls for the stained teeth; teeth "C" and "D" were treated with the carbamide peroxide as described above. Tobacco-stained teeth (tipper row in each photograph) and blood stained teeth (lower row in each photograph) are shown.

FIG. 3. FIG. 3A, before treatment; FIG. 3B, 4th day of treatment; FIG. 3C, 7th day of treatment. The photographs show teeth after staining by the chlorhexidine-tea model. (B and also C, D before treatment);

FIG. 4. FIG. 4A, before treatment; FIG. 4B, 4th day of treatment, FIG. 4C, 7th day of treatment. The discoloration was achieved by the blood staining method.

FIG. 5. FIG. 5A, before treatment; FIG. 5B, 4th day of treatment; FIG. 5C, 7th day of treatment. The discoloration of the teeth enamel was achieved by the chlorhexidine-tea method.

FIG. 6 shows the sustained-release of carbamide peroxide from films prepared from the liquid polymer composition of the invention.

FIG. 9. FIGS. 9A-9B (Photographs I and II, respectively) show the effect of treatment with 10% carbamide peroxide after 4 weeks (volunteer 194). FIG. 9A, time of treatment=0; FIG. 9B, time of treatment=4 weeks.

FIG. 10. FIGS. 10A-10B (Photographs I and II, respectively) show the effect of treatment with 10% carbamide peroxide after 4 weeks (volunteer 139). FIG. 10A, time of treatment=0; FIG. 10B, time of treatment=4 weeks.

DETAILED DESCRIPTION OF THE PREFERRED EMBODIMENTS

Figure 3A:
FIGS. 3A-3C (Photographs I, II, III, respectively) show the effect of bleaching with 3% carbamide peroxide liquid polymer of the invention (Teeth "C") and the same amount of peroxide in solution ("D") on discolored teeth after treatment for 4 and 7 days. Teeth "B" are controls for the stained teeth. Teeth "A" are clean teeth.
Figure 3B:
Figure 3C:

It is generally known that polymers are attacked by hydrogen peroxide or peroxy compounds, which are extremely active chemicals. This is especially a problem in hydroalcoholic solutions and has previously precluded the delivery of oxidizing agents from film compositions. In the present composition, surprisingly, apparently due to the presence of the stabilizing additive (such as, for example, calcium disodium edetate), the peroxides are stabilized when in hydroalcoholic solution. In addition, the cellulosic polymer appears to contribute to the stabilizing effect of the additive on the hydrogen peroxide and peroxy compounds. Therefore, the compositions of the invention are capable of delivering a desired concentration of an active peroxide component over a prolonged period of time from a film cellulosic polymer matrix.

It has been surprisingly found that the same composition of the invention that is useful for the delivery of oxidizing agents for the bleaching of teeth is also useful for the delivery of oxidizing agents for use as an antiplaque treatment, for the treatment of gingivitis and for other oral and periodontal diseases that response to a chemical oxidizing agent, in the same doses and application schedule as for tooth bleaching.

The composition of the invention has a surprisingly good oxidizing (and thus bleaching) efficiency. The composition of the invention is easy to use by the patient himself, and obviates the need to use casts or mouth guards. The composition of the invention is especially useful when it is desired or necessary to deliver a relatively low amount of an oxidizing agent. The composition of the invention does not injure the surrounding sensitive gingival tissue. In addition, the composition of the invention is useful for treating dental plaque, gingivitis and other oral and periodontal diseases that response to an oxidizing agent. Lastly and also importantly, the liquid polymer composition of the invention, containing the oxidizing agent, is very storage stable.

Accordingly, a patient afflicted with one or more dental conditions such as a need for tooth bleaching, dental plaque, gingivitis or other such conditions, can be accorded relief with one treatment regime, application of the composition of the invention, such treatment being performed in a manner that does not detract from the appearance of the patient and that is easily and quickly applied by the patient whether at home or away from home.

The liquid polymer composition of the invention introduces a new concept for treatment of biological conditions with peroxides. The liquid polymer is applied directly to the desired site and releases the active oxidizing agent in a sustained release manner, such release being of sufficient time to allow the oxidizing agent to achieve the desired biological effect.

The close contact between the active agent and the target site provides a very efficient method of treatment and prevents rapid decomposition of the peroxide in the oral cavity or other biological surface. Moreover, in view of the localization of the active agent, the required effective dose is much lower and, therefore, possible side effects associated with hydrogen or carbamide peroxides are minimal, if they even occur at all.

Other possible applications of the present liquid polymer composition are treatment of dental diseases, including periodontitis, treatment of minor oral infections, prevention of oral lesions, caries, and also as wound cleansing formulations. For example, the liquid polymer composition of the invention could be applied to a wound (or onto a bandage covering the wound) by the patient or his physician. The film that would form on the wound (or in the bandage) would then provide a sustained-release of the chemical oxidizing agent in a highly efficacious manner.

In detail, the invention provides a storage stable, sustained release liquid polymer composition comprising: (a) a water-soluble cellulosic polymer; and (b) a pharmaceutically or cosmetically acceptable oxidizing (sometimes called "bleaching") agent; in a pharmaceutically or cosmetically acceptable vehicle, wherein said sustained-release water-soluble, cellulosic polymer is selected from the group consisting of hydroxypropyl cellulose, hydroxypropyl ethylcellulose, hydroxypropyl methylcellulose, hydroxyethyl cellulose, hydroxyethyl methylcellulose and carboxymethyl-cellulose. Most preferable, a low viscosity form (lower molecular weight) of such polymers is used. Preferably, the polymer is hydroxypropyl cellulose. Such polymers may be commercially obtained. For example, hydroxypropyl cellulose useful in the compositions of the invention is sold as Klucel LF. Use of such hydroxypropyl cellulose eliminates the need to add strong chelating agents to the liquid polymer compositions which might destroy the mineralized structure of the tooth's enamel.

A pharmaceutically acceptable vehicle is one that will not harm the host and will not interfere with the chemical action of the polymer composition of the invention. A cosmetically acceptable vehicle is pharmaceutically acceptable but also does not detract from the appearance of the person or animal to which the composition has been applied. In a similar manner, a pharmaceutically acceptable oxidizing agent is one that will not harm the host viability at the concentrations being used and will not interfere with the chemical action of the polymer composition of the invention, but will impart a desired biological effect, such as an antibacterial effect. A cosmetically acceptable oxidizing agent is pharmaceutically acceptable but also does not detract from the appearance of the person or animal to which the composition has been applied.

Preferably, the liquid polymer oxidizing composition of the present invention additionally comprises a suitable pharmaceutically or cosmetically acceptable stabilizing additive. The additive should not alter the ability of the cellulosic polymer to form a film, should protect such film-forming capacity from attach by the peroxy compound, and should not precipitate other ingredients in the solution. Preferably this additive is soluble in hydroalcoholic solution and is selected from the group consisting of calcium disodium edetate, deferoxamine mesylate, tetrasodium edetate, citric acid and other suitable conventional additives, calcium disodium edetate being preferred over tetrasodium edetate as it is surprisingly superior to tetrasodium edetate as a stabilizing additive.

The oxidizing agent is preferably a peroxide compound selected from the group consisting of hydrogen peroxide, carbamide peroxide and sodium peroxyborate monohydrate, carbamide peroxide being particularly preferred.

The said pharmaceutically or cosmetically acceptable vehicle preferably comprises an agent selected from the group consisting of water, ethyl alcohol, and ethyl alcohol and water.

The liquid polymer composition of the present invention preferably contains from about 5% w/w to about 15% w/w hydroxypropyl cellulose, still more preferably 12.5% w/w hydroxypropyl cellulose. An equivalent amount of other polymers as described above may be used.

The liquid polymer composition of the present invention preferably contains from about 1% w/w to about 15% w/w carbamide peroxide, the concentration of 3% w/w carbamide peroxide being preferred for treating or preventing extrinsic discoloration, higher concentrations, from about 10 to about 15% w/w for treating or preventing intrinsic discoloration. An equivalent amount of other peroxy compounds as described above may be used.

As a stabilizer for the composition, the liquid polymer composition of the present invention preferably contains about 0.15% w/w calcium disodium edetate, deferoxamine mesylate, or tetrasodium edetate, and most preferably, calcium disodium edetate.

Water used in the compositions should be of a "purified" nature, distilled or deionized or both, such as that usually used in pharmaceutical preparations.

The liquid polymer oxidizing composition can be applied to the teeth directly, being a film-forming liquid polymer solution. The film is formed by the evaporation of the solvent and once coated onto the teeth or other surface the film the oxidizing agent in a sustained-release mode, and degrades within about one hour to disappearance, after delivery of the oxidizing agent. This time frame is sufficient to provide efficacious levels of the oxidizing agent. The liquid polymer can be applied to the teeth several times per day, depending on the severity of the discoloration.

The adherence of the film containing the oxidizing agent to the teeth provides for a very close contact between the tooth surface and the sustained-release oxidizing agent, resulting in very efficient removal of discolorations, notwithstanding the relatively low concentration of the oxidizing agent in the composition.

The present invention thus also provides a method of bleaching discolored teeth or preventing teeth discoloration comprising topical application of the liquid polymer composition of the present invention to the teeth of a human or an animal.

In the method of bleaching discolored teeth the liquid polymer composition of the invention is preferably applied to the teeth from once to three times per day, according to the severity of discoloration and the attending dentist's recommendations.

The method of preventing teeth discoloration according to the present invention is intended for individuals apt to develop tooth discoloration, for example, individuals using chlorhexidine-containing dental preparations (for treatment of gingivitis, etc.), smokers, individuals with teeth susceptible to staining by tea and like. In this method the liquid polymer of the present invention is applied to the teeth once or twice per week, as required and/or recommended by the attending dentist.

For all these treatments of extrinsic discolorations, caused for example by nicotine, tea, etc., a concentration of 3% carbamide peroxide has been found adequate.

In addition, the liquid polymer according to the present invention may be used by dentists for bleaching intrinsically stained teeth and for non-vital bleaching. The liquid polymer of the present invention can be used in known non-vital bleaching techniques to replace the peroxide solution which is introduced to the tooth pulp chamber. The leakage, the free diffusion and the concomitant undesirable cervical resorption associated with such techniques, can all be avoided by introducing the liquid polymer composition of the present invention into the pulp chamber, instead of the peroxide solution, drying to a film with a stream of air, and sealing conventionally. A 10–15% carbamide concentration is adequate for the intrinsic discolorations. Where applied to root canals, the peroxide is released into the pulp chamber, while the formed polymeric film would remain in situ, the surroundings being essentially water-free.

As stated above, the presently available commercial bleaching products and the conventional techniques for tooth bleaching are inconvenient and of limited use. It appears that the enamel surfaces are not receptive to bleaching agents delivered by solutions and gels, especially when the dentin is involved and the discoloration is deep inside cracks and pits in the enamel. As will be shown hereafter, the presently claimed sustained-release bleaching liquid polymer is an efficacious dental product, facilitating tooth bleaching and rendering this treatment safer and more efficient, less time-consuming and improving patient compliance. The active bleaching agent is released over a period of about 10 to 30 minutes. This constitutes an advantage since results are achieved over a relatively short 2period of time, minimizing possible damage to the surrounding gingival tissue. Additionally, the storage stability and long shelf life of the composition are, as stated, a prominent advantage, particularly in view of the fact that hydrogen peroxide and peroxide compounds, which are very powerful chemicals, are known to attack cellulosic polymers per se. However, as used in the present composition, not only is the polymer not attacked, but the concentration of the peroxy component does not decrease over long period of storage. Instead of the peroxide attacking the polymer, the polymer appears to stabilize the peroxide. This effect is surprising and unexpected. The optional stabilizing additive apparently further contributes to the improved stability.

Additionally, there is minimal inconvenience to the patient. It is not necessary that the patient wear any device that would detract from the patient's cosmetic appearance. In addition, unlike foams, the patient may apply the polymer of the invention and forget about it. A bleaching foam requires that the patient apply, wait (often for about 5 minutes) and rinse off the foam product, all the time attempting to keep his lips and skin tissue in the oral cavity from coming in contact with the bleaching foam preparation. According to the invention, this is not necessary, as, even when the polymer composition of the invention comes in contact with the tissue and skin in the dental area, such tissue and skin are not harmed by the polymer composition of the invention.

The liquid polymer oxidizing composition of the present invention, in the same embodiments and manner of treatment as for bleaching teeth, is also intended for use in the treatment or prevention of oral and/or dental diseases or conditions. For example, plaque and caries are among the dental diseases or conditions which may be treated or prevented through the application of the liquid polymer composition of the present invention. The composition of the invention, when utilized for its anti-plaque properties, will be provided in an effective anti-plaque amount to a recipient, such amounts being the same as those for bleaching of the teeth. Such composition is then capable of preventing or attenuating the accumulation of plaque or caries. The oral composition of the invention assists in the prevention of dental caries and periodontal disease, and in the relief of symptoms resulting from existing gingival and subgingival problems, by attacking the pathogenic bacteria responsible for plaque formation and consequent cariotic and periodontal diseases.

The composition effective for the treatment or prevention of plaque, dental caries or periodontal disease is such that the oxidizing agent acts as the antibacterial agent, and can be released in a sustained fashion, has the property of adhesion to the gums and teeth, and such that the antibacterial composition remains plastic during the entire period of application.

It is also a feature of this invention that the aforementioned bacteriocidal oxidizing agent is released to the sites of carious lesions and periodontal pockets in a sustained release manner. The compositions of the invention, being especially efficient at stabilizing the peroxide agent, can provide amounts of peroxide compounds that are not damaging to the soft dental tissues, but yet are sufficiently high to provide for the desired antibacterial effect.

The compositions of the invention are especially useful in the treatment of gingivitis and dental plaque in animals, and especially pets. The major cause of death in the United States of dogs and cats over four years old is starvation due to tooth loss. The composition of the invention can be applied to the teeth of animals with an applicator, so as to help treat or prevent against gingivitis-induced or plaque-induced tooth loss.

Having now generally described the invention, the same will become better understood by reference to certain specific examples which are included herein for purposes of illustration only and are not intended to be limiting unless other wise specified. In general, two extrinsic staining models of extracted teeth, using tobacco and chlorhexidine, and one intrinsic model using human blood will be demonstrated.

EXAMPLES

Example 1

Experimental Methods

Two liquid polymer preparations were prepared and tested, one containing 1.25% carbamide, peroxide and the other 3.0% of this agent.

TABLE I

| Ingredients: | (% w/w) | (% w/w) |
| --- | --- | --- |
| Carbamide peroxide | 3.00 | 1.25 |
| Tetrasodium edetate | 0.15 | 0.15 |
| Hydroxypropyl cellulose | 12.50 | 12.50 |
| Ethyl alcohol | 60.00 | 61.00 |
| Purified water | 24.35 | 25.10 |

In a further series of experiments, the following preparations were made:

TABLE II

| INGREDIENT | % w/w | | | |
| --- | --- | --- | --- | --- |
| | 3 | 6 | 8 | 10 |
| Carbamide peroxide | 3.6 | 6.0 | 8.0 | 10.0 |
| Edetate calcium disodium | 0.10 | 0.10 | 0.10 | 0.10 |
| Hydroxypropyl cellulose | 12.45 | 12.45 | 12.45 | 12.45 |
| Ethyl alcohol | 53.32 | 51.8 | 50.50 | 49.25 |
| Purified water | 30.53 | 29.65 | 28.95 | 28.20 |

Carbamide peroxide and the edetate salt are dissolved in purified water. Ethyl alcohol is added to the solution and hydroxypropyl cellulose is added in small portions until completely dissolved. The viscosity of the solution obtained is about 4,000 cps (centipoise).

Release of Peroxide from Liquid Polymer

In order to examine the peroxide sustained-release formulations, films were prepared and studied for the in vitro peroxide release into physiological 0.02M phosphate buffer, pH 6.8, at 37° C.

Film preparation: 3 grams of the liquid formulations containing 1.25% (w/w) and 3.0% (w/w) carbamide peroxide were poured onto separate teflon plates (6.5 cm in diameter). The plates were allowed to dry for 15 hours at 4° C.

In vitro release: The films which were formed on the plates were then cut to circles of 1 cm diameter and accurately weighed. Film sample replicates (six) were placed in vials containing 5 ml phosphate buffer (0.02M, pH 6.8 and 0.002 ml Dequest® 2066 (Diethylene-triaminepenta(methylenephosphonic acid), Monsanto, Newport, Gwent, U.K.). Another sample was analyzed for water content by loss on drying method (USP XXII p. 1568). The release of the peroxide from the degradable films was carried out at 37° C. in a shaker bath (30 strokes/minutes). Aliquots (1 ml) were taken from the vials at pre-determined time intervals. 0.2 ml samples were transferred into separated tubes and analyzed for peroxide concentration using the method as described below.

Measurement of Carbamide Peroxide Content In Liquid Polymer

A colorimetric assay was used for the quantitative determination of carbamide peroxide. The following assay (modification of a method published by Ito et al., *J. Assoc. Off. Anal. Chem.* 64: 1448–1452 (1981)) utilized horseradish peroxidase which catalyzed hydrolysis of peroxide in the presence of the chromogenic hydrogen donor 4-aminoantipyrine. The assay is sensitive, rapid and reproducible.

Specimens (0.5 g) of the liquid polymer preparation were accurately weighed in 50 ml volumetric flasks, and volume was made up 50 ml with ethanol. Samples (0.2 ml) were introduced into 13×100 mm test tubes, followed by the addition of:

1. 0.8 ml water;
2. 1 ml 0.4M Tris-HCl buffer containing $4 \times 10^{-3}$M $MgCl_2$ and $4 \times 10^{-4}$M $ZnCl_2$, pH 8.3;
3. 2 ml 0.17M aqueous phenol containing $2.5 \times 10^{-3}$M 4-aminoantipyrine; and
4. 0.02 ml peroxidase solution (activity 600 purpurogalin units/ml).

The tubes were: sealed, vortexed and incubated at 37° C. for 25 minutes, then centrifuged at 4,000 rpm for 5 minutes. The color developed was measured by a UV/VIS spectrophotometer at 510 nm against a blank solution, and compared to standard solutions prepared in the same method.

Example 2

In vitro Bleaching of Discolored Teeth

1. Preparation of the Staining Models

All extracted teeth were scaled to remove calculus and periodontal tissue residuals, soaked in sodium hypochlorite solution (3 g available chlorine/liter) for 24 hours, then washed and dried.

A. Blood Staining

Three anterior teeth were stained using whole blood in a high speed centrifuge, as described by Freccia and Peters, *J. Endodont.* 3: 6709 (1982). The teeth were each incubated in separate tubes containing human whole blood at 35° C. Twice a day, for three consecutive days, the tubes were centrifuged for 20 minutes at 2500 rpm. Thereafter, the teeth were rinsed with purified water, then transferred into fresh blood tubes and the procedure repeated for 3 additional days. Before photographing, the teeth were washed and dried.

B. Tobacco Staining

Three anterior teeth were put in a suction flask containing 10 ml of purified water. The smoke from ten cigarettes whose filters were removed, was suctioned into the water by weak pumping. The teeth were left in the tobacco-smoked water for 24 hours, then washed, dried and photographed.

C. Chlorhexidine-Tea Staining

Chlorhexidine alone does not cause tooth staining in vitro. However, it does stain in the presence of other substances or food ingredients, such as soiree found in tea (Addy et al. *IRCS Medical Science* 5: 393 (1977)).

Three anterior tee, th were incubated for 2 hours in a 2% chlorhexidine gluconate solution, washed with purified water and then further incubated for 30 minutes in 100 ml of tea made from 3 tea bags each containing 1 g regular tea. The whole procedure was repeated 5–6 times a day for 3 consecutive days. During nights the teeth were stored in the 2% chlorhexidine solution.

2. The Bleaching Process

The discolored tooth was dipped in the liquid polymer according to the formulation given above for 1 second, then allowed to dry for not more than 15 minutes (3–5 minutes are usually sufficient). The tooth was weighed before dipping and after drying to determine the carbamide peroxide pickup. Thereafter, the tooth was immersed in 5 ml of a 0.02M phosphate buffer (pH 6.8) at 37° C. for 45 minutes. A control experiment of bleaching was performed on another discolored tooth in phosphate buffer containing the exact amount of carbamide peroxide which was picked-up on the liquid polymer coated tooth.

One day of treatment was defined as three consecutive bleaching processes. All the experiments terminated on the seventh day, even if complete bleaching has been noted before. The shade/brightness of the enamel after each daily treatment was assessed according to the VITA Lumin® Vacuum shade guide system (W. Germany).

RESULTS AND CONCLUSIONS

Pictures of the teeth are shown in FIGS. 1–5. The in vitro release profiles of 1.25% (w/w) and 3% (w/w) peroxide containing formulations are shown in FIG. 6. Table I summarizes the stability of peroxide in the liquid polymer formulation. The bleaching effect of the liquid polymer (containing 3% carbamide peroxide) on the enamel against comparable carbamide peroxide solution is presented in Table IV.

Example 3

In Vitro Release and Stability

The examination of peroxide release from the liquid polymer films (FIG. 6) into buffer was not simple, because the peroxide compound tended to decompose in warmed aqueous solutions. By adding 0.4% (w/w) Dequest 2066 to the solutions, decomposition was reduced and a considerable recovery of the agent was achieved. As may be seen from FIG. 6, the peroxide was released from the films during 30 minutes, without any significant change in the cumulative release between the two concentrations tested. However, it was noticed that at the higher peroxide concentration, the film was softer and "stickier", and it adhered to teeth with greater ease.

A stability study performed at room temperature showed (Table III) that the peroxide containing liquid polymer formulation was stable during the period of the study (5 months). It should be noted that it is usually recommended to store products containing peroxides at 0°–5° C. However, while there is no complicated problem in cooling the bleaching liquid polymer to such low temperatures, it is evidently a great advantage that the composition may be stored at ambient temperature, retaining stability if carried to work during travel etc. and used when required. As stated in the description, this good stability of the composition is one of its prominent advantages. Proper laboratory grade glass containers and applicators such be used, to avoid too high levels of heavy metals' impurities.

Example 4

Effect of Sustained-release Peroxide vs. Peroxide Solution on Tooth Bleaching

In all the experiments concerning the evaluation of the bleaching liquid polymer as compared with a peroxide solution, the 3% peroxide formulation was used. A prominent difference between the efficacy of the bleaching liquid polymer and that of the comparable peroxide solution was visually observed. This favorable difference of the liquid polymer, which constitutes another important advantage of the invention, could be noticed after 4 and 7 days in all the three models tried for staining.

Figure 4A:
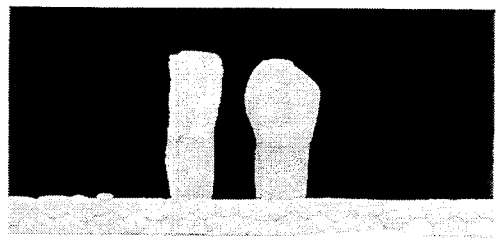
FIGS. 4A-4C (Photographs I, II, III) show the effect of bleaching with 3% carbamide peroxide liquid polymer of the invention (left tooth in each photograph) and the same amount of peroxide in solution (right tooth in each photograph) on discolored enamel after treatment for 4 and 7 days.
Figure 4B:
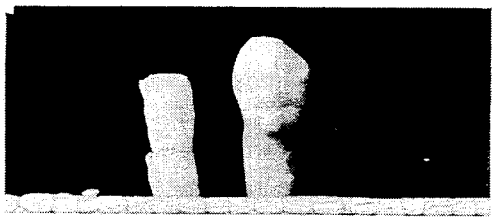
Figure 4C:
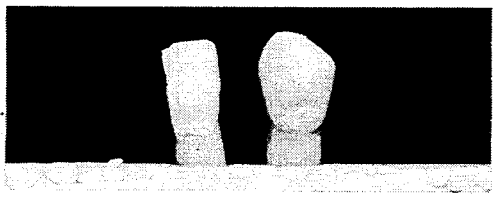
Figure 5A:
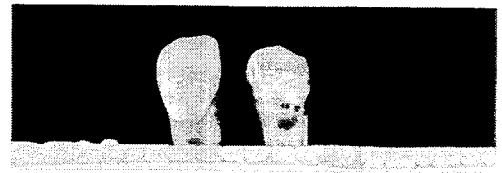
FIG. 5A-5C (Photographs I, II, III, respectively) show the effect of bleaching with 3% carbamide peroxide liquid polymer of the invention (left tooth in each photograph) and same amount of peroxide in solution (right tooth in each photograph) on discolored enamel after treatment for 4 and 7 days.
Figure 5B:
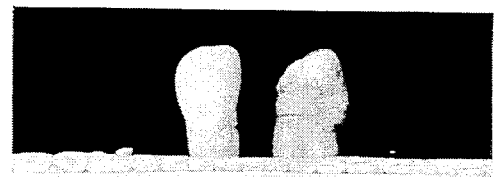
Figure 5C:

A more precise visual evaluation and comparison of the effect of bleaching processes was made on the teeth enamel by using the shade/brightness guide system. As may be seen from Table V, the best result in enamel whitening was achieved by the liquid polymer that as applied onto a chlorhexidine stained tooth. The brightness of this tooth improved by 15 degrees and more, while the peroxide solution improved the enamel brightness by only 7 degrees. As for the blood and the tobacco models, the enamel brightness raised by 6 and 5 degrees, respectively, when liquid polymer was used, as compared with 2 and 3 degrees, respectively, when the peroxide solution was used. FIGS. 4 and 5 present the crowns of the teeth (from left to right) after treatment with the liquid polymer of the invention and the comparative peroxide solution, and demonstrate the significant improvement in the brightness of the crowns when using the bleaching liquid polymer.

TABLE III

The Stability of Peroxide in the Bleaching Liquid Polymer Stored at Room Temperature

| Storage time | Concentration found, % | |
|---|---|---|
| (days) | Product A* | Product B* |
| 0 | 1.33 | 3.13 |
| 3 | 1.33 | — |
| 30 | — | 3.02 |
| 100 | — | 3.00 |
| 155 | 1.31 | — |

*Product A contained theoretically a concentration of 1.25% carbamide peroxide, and Product B contained 3.0% carbamide peroxide.

TABLE IV

The improvement in enamel brightness using 3% peroxide contained liquid container liquid polymer and a comparable peroxide solution

| Treatment period | Discoloration Model Used | | | | | |
|---|---|---|---|---|---|---|
| | Tobacco | | Blood | | Chlorbexidine | |
| (days) | LP* | Sol | LP | Sol | LP | Sol |
| 0 | C1 | C1 | A3 | A3 | >C4 | >C4 |
| 1 | D2 | A2 | C1 | A3 | C1 | C4 |
| 2 | D2 | A2 | C1 | A3 | A2-C1 | A4 |
| 3 | A1 | A2 | C1 | C2 | A1 | A3 |
| 4 | B1 | A2 | A2-C1 | C2 | A1 | A3 |
| 5 | B1 | A2 | A2 | C2 | B1 | A3 |
| 6 | B1 | A2 | A2 | C2 | B1 | A3 |
| 7 | B1 | B2 | B3 | C2 | >B1 | A3 |

*LP = 3% peroxide-containing liquid polymer;
Sol = solution containing same amount of peroxide loaded on the LP tooth Decreasing Order of the brightness Degrees:
B1..A1    B2..D2..A2..C1..C2..D4..A3..B3-..A3.5..B4..C3..A4..C4.

Example 5

In Vivo Bleaching of the Stained Teeth-Clinical Study

1. Study Design

In a double blind study, the efficiency of two formulations containing different concentrations of carbamide peroxide (UP), 3% and 10% w/w, was evaluated. The formulations used for the clinical trial are show in Table V.

TABLE V

| Ingredients: | (% w/w) | (% w/w) |
|---|---|---|
| Carbamide peroxide | 3.00 | 10.00 |
| Edetate tetrasodium (tetrahydrate) | 0.10 | 0.10 |
| Hydroxypropyl cellulose | 12.40 | 12.45 |
| Ethyl alcohol | 60.00 | 54.75 |
| Purified water | 24.50 | 22.70 |

Twenty nine subjects were randomly assigned to one of two groups. Fifteen people applied the 3% UP formulation of Table V on their front tooth, and 14 applied the 10% UP formulation of Table V. Both groups used the liquid polymer 3 times a day for 4 weeks. Examinations were performed on the first day (t=0), and after 1, 2 and 4 weeks. At each time of examination, each patient's teeth were photographed and the staining was scored. The scoring was performed according to the Lobene Extrinsic Tooth Stain Index (R. R. Lobene, *J. Am. Dent. Assoc.* 77: 849–855 (1968)), in which the tooth was divided to body and gingival regions, each evaluated for staining area and intensity. The multiplication of the area and intensity scores of each region, which yields the stain index score, indicates the severity of the stain.

2. Statistical Analysis

In order to evaluate the clinical results two test methods were carried out:

1. The Paired Sample Wilcoxon Signed Rank Test was used to analyze the differences between scores at the various treatment periods within groups.
2. The comparison between the 3% UP-treated and the 10% UP-treated groups was made by unpaired tests. First, the Ansari-Bradley Test for equality of dispersion was performed. If the data samples were found to have equal dispersion, a nonparametric test of significance was proceeded using the Wilcoxon Rank Sum Test (Mann-Whitney Test).

It should be noted that the paired-sample test was used on the severity scores (Lobens Stain Index scores), while the unpaired sample test was performed on the scores after normalizing them to baseline.

3. Results

Figure 7:
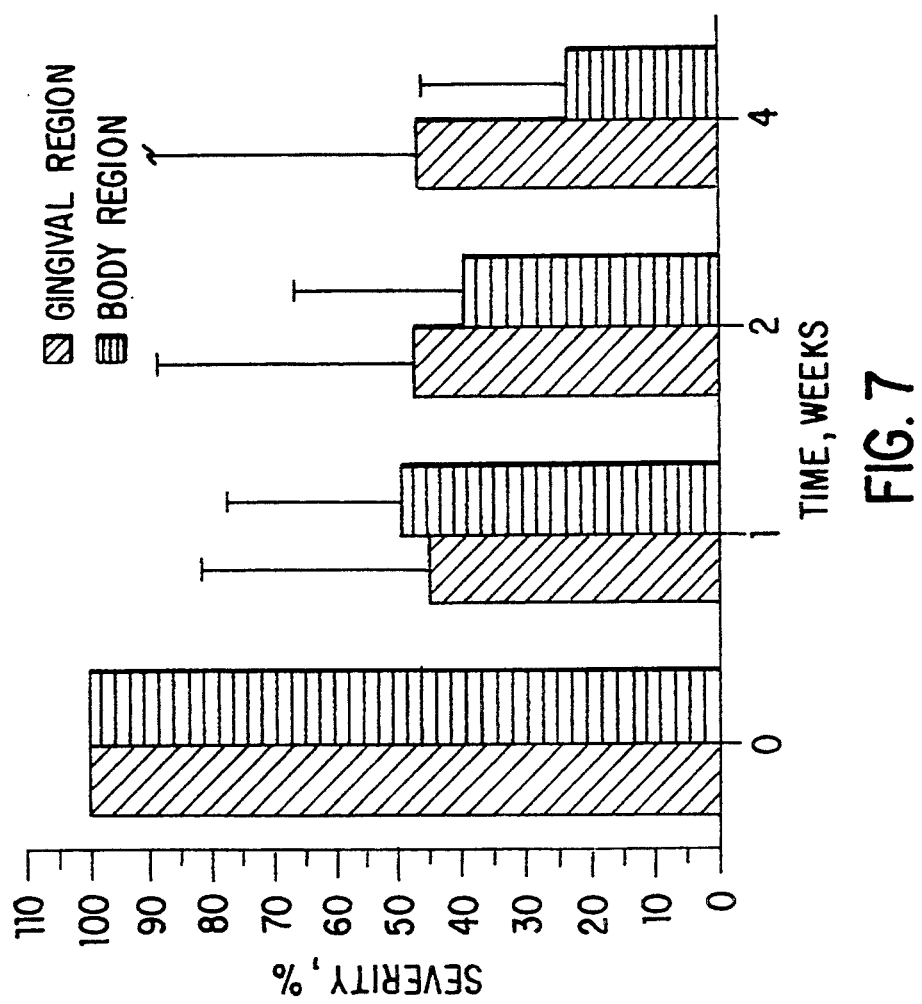
FIG. 7 shows the decrease in severity of teeth staining with treatment of the liquid polymer of the invention (3% urea peroxide).
Figure 8:
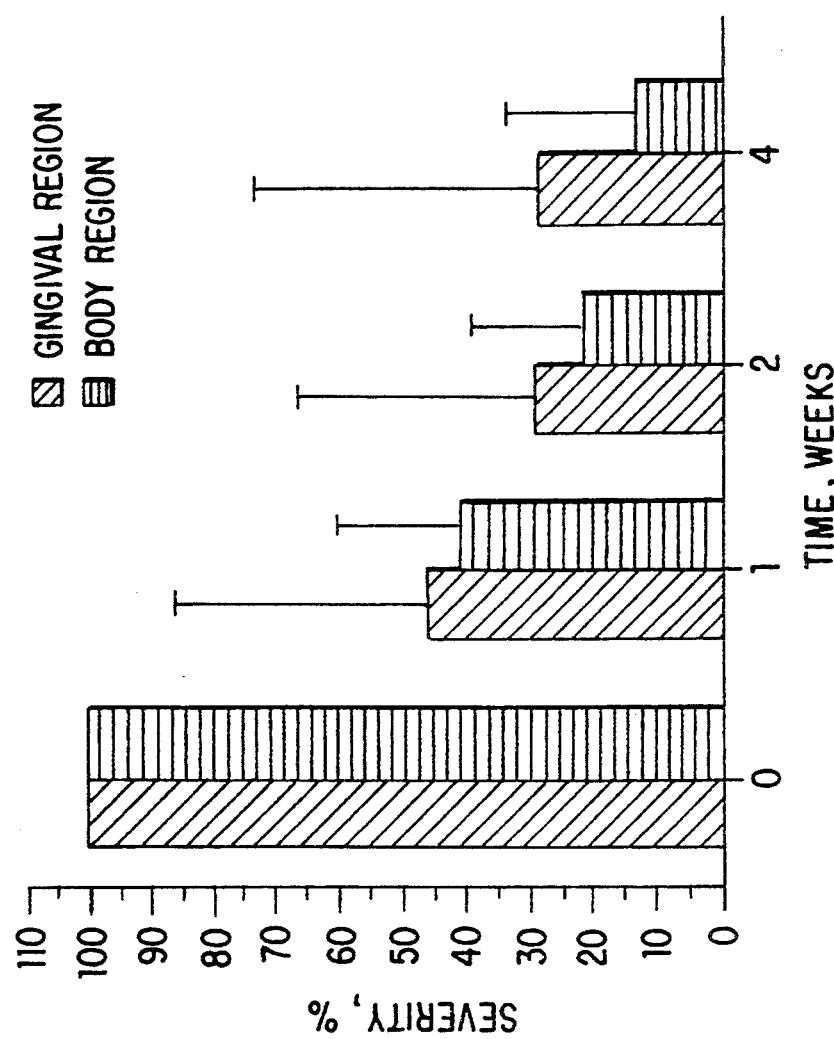
FIG. 8 shows the decrease in severity of teeth staining with treatment of the liquid polymer of the invention (10% urea peroxide).

Tables VI and VII show the mean Lobene Stain Index scores (±standard deviation), for each tooth region in the two groups studied. A marked drop in the severity of the staining condition was observed from the first week and onward in the two groups. This evident since the difference between the scores of each week (1, 2, 4) and baseline scores was statistically significant (see Tables). Furthermore, the significant difference between week 4 and week 1 in the body region of the teeth (also, week 2 and week 1 in the 10%-UP group) proves that the treatment is more effective over time, and at least in the body region there is a consistent drop during the 4-week study. FIGS. 7 and 8, and also FIGS. 9 and 10 (photographs) illustrate the reduction in straining severity for each group. No particular difference was noted between the groups, except that the normalized scores in the teeth's body region of the 10%-UP group was significantly different from those of the 3%-UP group only at week 2.

It is thus concluded that:

1. The tooth Bleaching Liquid Polymer has been proved to be very efficacious in whitening extrinsic staining, when applied 3 times a day for 1 week, the efficiency increases with longer use.
2. The Liquid Polymer's bleaching action could be effectively performed in use of a wide range of urea peroxide concentrations, starting from a minimum of 3%.

TABLE VI

Severity of Teeth Staining in a 3% Urea Peroxide Group

| Time, wks. Gingival Region | | Difference as compared* within group after week: | | | |
|---|---|---|---|---|---|
| Mean | S.D. | 0 | 1 | 2 | 4 |
| 0  10.69 | 8.84 | — | HS | VS | S |
| 1   5.61 | 6.65 | — | — | NS | NS |
| 2   5.77 | 7.39 | — | — | — | NS |
| 4   5.42 | 6.75 | — | — | — | — |

| Time, wks. Body Region | | Difference as compared* within group after week: | | | |
|---|---|---|---|---|---|
| Mean | S.D. | 0 | 1 | 2 | 4 |
| 0  11.80 | 7.16 | — | NS | HS | HS |
| 1   5.47 | 3.94 | — | — | NS | VS |
| 2   4.78 | 3.80 | — | — | — | NS |
| 4   3.61 | 4.09 | — | — | — | — |

*The difference in scores between the weeks (wks) of treatment within each group was tested for significance by using the Wilcoxon Signed Rank Test (two-tailed). Statistical significance (S) was based on $p < 0.05$. Very significant difference (VS) was determined when $p < 0.01$, while high significance (HS) was indicated in case of $p < 0.001$.

TABLE VII

Severity of Teeth Staining in a 10% Urea Peroxide Group

| Time, wks. Gingival Region | | Difference as compared* within group after week: | | | |
|---|---|---|---|---|---|
| Mean | S.D. | 0 | 1 | 2 | 4 |
| 0  13.69 | 9.42 | — | VS | HS | HS |
| 1   6.15 | 6.67 | — | — | NS | NS |
| 2   3.86 | 4.27 | — | — | — | NS |
| 4   4.28 | 5.00 | — | — | — | — |

| Time, wks. Body Region | | Difference as compared* within group after week: | | | |
|---|---|---|---|---|---|
| Mean | S.D. | 0 | 1 | 2 | 4 |
| 0  10.69 | 4.17 | — | HS | HS | HS |
| 1   4.75 | 3.05 | — | — | VS | VS |
| 2   2.54 | 2.40 | — | — | — | NS |
| 4   1.84 | 2.44 | — | — | — | — |

[8]The difference in scores between the weeks of treatment within each group was tested for significance by using the Wilcoxon Signed Rank Test (two-tailed). Statistical significance (S) was based on $p < 0.05$. Very significant difference (VS) was determined when $p < 0.01$, while high significance (HS) was indicated in case of $p < 0.001$.

Having now fully described the invention, it will be understood by those with skill in the art that the scope may be performed with a wide and equivalent range of concentrations, parameters, and the like, without affecting the spirit or scope of the invention or any embodiment thereof.

What is claimed is:

1. A sustained-release film-forming liquid polymer composition comprising:
   (a) a film-forming amount of a water-soluble cellulosic polymer;
   (b) an efficacious amount of a pharmaceutically acceptable peroxy compound;
   (c) a pharmaceutically acceptable stabilizing additive which is soluble in hydroalcoholic solution, is selected from the group consisting of citric acid, a deferoxamine mesylate, and an edetate salt of an alkaline-earth metal, and is present in an amount sufficient to stabilize said peroxy compound in the presence of said polymer; and
   (d) a pharmaceutically acceptable vehicle, wherein said film-forming liquid polymer composition is stable at ambient temperature for at least 30 days.

2. The liquid polymer composition of claim 1 wherein said water-soluble cellulosic polymer is selected from the group consisting of hydroxypropyl cellulose, hydroxypropyl ethylcellulose, hydroxypropyl methylcellulose and carboxymethylcellulose.

3. The liquid polymer composition of claim 2 wherein said pharmaceutically acceptable stabilizing additive is selected from the group consisting of calcium disodium edetate, tetrasodium edetate, deferoxamine mesylate and citric acid.

4. The liquid polymer composition of claim 3 wherein said pharmaceutically acceptable stabilizing additive is calcium disodium edetate.

5. The liquid polymer composition of any one of claims 1–4 wherein said peroxy compound is selected from the group consisting of hydrogen peroxide, carbamide peroxide, and sodium peroxyborate monohydrate.

6. The liquid polymer composition of claim 5, wherein said peroxy compound is carbamide peroxide.

7. The liquid polymer composition of claim 6, wherein said carbamide peroxide is present in an amount of from about 1% w/w to 15% w/w.

8. The liquid polymer composition of any one of claims 1–4 wherein said pharmaceutically acceptable vehicle is selected from the group consisting of water, ethyl alcohol, and ethyl alcohol and water.

9. The liquid polymer composition of any one of claims 1–4, wherein said polymer is hydroxypropyl cellulose.

10. The liquid polymer composition of claim 9 containing from about 5% w/w to about 15% w/w hydroxypropyl cellulose.

11. The liquid polymer composition of claim 10 containing 12.5% w/w hydroxypropyl cellulose.

12. The liquid polymer composition of claim 4 comprising about 12.5% w/w hydroxypropyl cellulose, about 3.00% w/w carbamide peroxide, about 0.15% w/w calcium disodium edetate, 60% w/w ethyl alcohol and purified water up to 100% w/w.

13. A method of extrinsically bleaching teeth, comprising topically applying the liquid polymer composition of any one of claims 1 to 4 or 12 to the teeth of a human or an animal.

14. The method of extrinsically bleaching discolored teeth of claim 13 wherein said liquid polymer composition is applied to the teeth from one to three times a day.

15. A method of preventing extrinsic teeth discoloration, comprising topical application of the liquid polymer composition of any one of claims 1 to 4 or 12 to the teeth of a human or an animal.

16. The method of preventing teeth discoloration according to claim 15 wherein said liquid polymer composition is applied to the teeth once or twice a week.

17. A method for bleaching intrinsically discolored teeth comprising introducing the liquid polymer composition of any one of claims 1 to 4 or 12 to the pulp chamber of the teeth of a human or animal.

18. The method of claim 17, wherein said liquid polymer composition introduced into the tooth pulp chamber is sealed therein.

19. A method for treating gingivitis comprising topical application of the liquid polymer composition of any one of claims 1 to 4 or 12 to the teeth of a human or an animal.

20. The method of treating gingivitis of claim 19, wherein said liquid polymer composition is applied to the teeth from one to three times a day.

21. The method of treating gingivitis according to claim 19, wherein said liquid polymer composition is applied to the teeth once or twice a week.

22. A method for treating dental plaque comprising topically applying the liquid polymer composition of any one of claims 1 to 4 or 12 to the teeth of a human or an animal.

23. The method of treating dental plaque of claim 22, wherein said liquid polymer composition is applied to the teeth from one to three times a day.

24. The method of treating dental plaque according to claim 22, wherein said liquid polymer composition is applied to the teeth once or twice a week.

25. The method of claim 13 wherein said peroxy compound of said liquid polymer composition is selected from the group consisting of hydrogen peroxide, carbamide peroxide, and sodium peroxyborate monohydrate.

26. The method of claim 25 wherein said peroxy compound is carbamide peroxide.

27. The method of claim 26 wherein said carbamide peroxide is present in an amount of from about 1% w/w to about 15% w/w.

28. The method of claim 13 wherein said pharmaceutically acceptable vehicle of said liquid polymer composition is selected from the group consisting of water, ethyl alcohol, and ethyl alcohol and water.

29. The method of claim 13 wherein said cellulosic polymer of said liquid polymer composition is hydroxypropyl cellulose.

30. The method of claim 29 wherein said hydroxypropyl cellulose is present in an amount of from about 5% w/w to about 15% w/w.

31. The method of claim 30 wherein said hydroxypropyl cellulose is present in an amount of about 12.5% w/w.

32. The method of claim 15 wherein said peroxy compound of said liquid polymer composition is selected from the group consisting of hydrogen peroxide, carbamide peroxide, and sodium peroxyborate monohydrate.

33. The method of claim 32 wherein said peroxy compound is carbamide peroxide.

34. The method of claim 33 wherein said carbamide peroxide is present in an amount of from about 1% w/w to about 15% w/w.

35. The method of claim 15 wherein said pharmaceutically acceptable vehicle of said liquid polymer composition is selected from the group consisting of water, ethyl alcohol, and ethyl alcohol and water.

36. The method of claim 15 wherein said cellulosic polymer of said liquid polymer composition is hydroxypropyl cellulose.

37. The method of claim 36 wherein said hydroxypropyl cellulose is present in an amount of from about 5% w/w to about 15% w/w.

38. The method of claim 37 wherein said hydroxypropyl cellulose is present in an amount of about 12.5% w/w.

39. The method of claim 17 wherein said peroxy compound of said liquid polymer composition is selected from the group consisting of hydrogen peroxide, carbamide peroxide, and sodium peroxyborate monohydrate.

40. The method of claim 39 wherein said peroxy compound is carbamide peroxide.

41. The method of claim 40 wherein said carbamide peroxide is present in an amount of from about 1% w/w to about 15% w/w.

42. The method of claim 17 wherein said pharmaceutically acceptable vehicle of said liquid polymer composition is selected from the group consisting of water, ethyl alcohol, and ethyl alcohol and water.

43. The method of claim 17 wherein said cellulosic polymer of said liquid polymer composition is hydroxypropyl cellulose.

44. The method of claim 43 wherein said hydroxypropyl cellulose is present in an amount of from about 5% w/w to about 15% w/w.

45. The method of claim 44 wherein said hydroxypropyl cellulose is present in an amount of about 12.5% w/w.

46. The method of claim 19 wherein said peroxy compound of said liquid polymer composition is selected from the group consisting of hydrogen peroxide, carbamide peroxide, and sodium peroxyborate monohydrate.

47. The method of claim 46 wherein said peroxy compound is carbamide peroxide.

48. The method of claim 47 wherein said carbamide peroxide is present in an amount of from about 1% w/w to about 15% w/w.

49. The method of claim 19 wherein said pharmaceutically acceptable vehicle of said liquid polymer composition is selected from the group consisting of water, ethyl alcohol, and ethyl alcohol and water.

50. The method of claim 19 wherein said cellulosic polymer of said liquid polymer composition is hydroxypropyl cellulose.

51. The method of claim 50 wherein said hydroxypropyl cellulose is present in an amount of from about 5% w/w to about 15% w/w.

52. The method of claim 51 wherein said hydroxypropyl cellulose is present in an amount of about 12.5% w/w.

53. The method of claim 22 wherein said peroxy compound of said liquid polymer composition is selected from the group consisting of hydrogen peroxide, carbamide peroxide, and sodium peroxyborate monohydrate.

54. The method of claim 53 wherein said peroxy compound is carbamide peroxide.

55. The method of claim 54 wherein said carbamide peroxide is present in an amount of from about 1% w/w to about 15% w/w.

56. The method of claim 22 wherein said pharmaceutically acceptable vehicle of said liquid polymer composition is selected from the group consisting of water, ethyl alcohol, and ethyl alcohol and water.

57. The method of claim 22 wherein said cellulosic polymer of said liquid polymer composition is hydroxypropyl cellulose.

58. The method of claim 57 wherein said hydroxypropyl cellulose is present in an amount of from about 5% w/w to about 15% w/w.

59. The method of claim 58 wherein said hydroxypropyl cellulose is present in an amount of about 12.5% w/w.

* * * * *